(12) United States Patent
Ooida (10) Patent No.: US 8,079,360 B2
(45) Date of Patent: Dec. 20, 2011

(54) INHALER

(75) Inventor: Junichi Ooida, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 980 days.

(21) Appl. No.: 12/031,286

(22) Filed: Feb. 14, 2008

(65) Prior Publication Data

US 2008/0216824 A1 Sep. 11, 2008

(30) Foreign Application Priority Data

Mar. 6, 2007 (JP) ................................. 2007-055023

(51) Int. Cl.
*A61M 11/00* (2006.01)
*B05B 17/06* (2006.01)
(52) U.S. Cl. .............................. 128/200.14; 128/200.16
(58) Field of Classification Search ............ 128/200.14, 128/200.16, 200.21–200.24, 203.12, 203.14, 128/204.21; 222/52, 54, 310
See application file for complete search history.

(56) References Cited

U.S. PATENT DOCUMENTS

| 6,923,179 B2 * | 8/2005 | Gupta et al. ............. 128/203.17 |
| 2008/0092880 A1 | 4/2008 | Ooida et al. ............. 128/200.14 |

FOREIGN PATENT DOCUMENTS

| WO | 95/01137 A1 | 1/1995 |
| WO | 96/09846 A1 | 4/1995 |
| WO | 00/24362 A1 | 5/2000 |
| WO | 2002/004043 A1 | 1/2002 |

* cited by examiner

*Primary Examiner* — Kristen Matter
(74) *Attorney, Agent, or Firm* — Fitzpatrick, Cella, Harper & Scinto (57) ABSTRACT

An inhaler, capable of inhaling liquid droplets having a constant diameter regardless of use environments, for making a user inhale medicine from a suction port has: an air flow path connected with the suction port and for passing the medicine through; an opening mounted with a medicine ejection portion for ejecting the medicine and formed at a part of the air flow path so that the ejected medicine is ejected in the air flow path; a flow path length determining portion for determining a distance from the opening to the suction port according to use environments in using the inhaler; and a flow path length adjustable mechanism capable of changing the distance from the opening to the suction port.

5 Claims, 7 Drawing Sheets

| L [m] | | H (%) | | | | | | | | |
|---|---|---|---|---|---|---|---|---|---|---|
| Tg [°C] | | 5 | 15 | 25 | 35 | 45 | 55 | 65 | 75 | 85 |
| | 5 | 0.229 | 0.256 | 0.290 | 0.334 | 0.394 | 0.481 | 0.618 | 0.864 | 1.438 |
| | 10 | 0.160 | 0.179 | 0.203 | 0.233 | 0.275 | 0.336 | 0.431 | 0.602 | 1.002 |
| | 15 | 0.114 | 0.127 | 0.143 | 0.165 | 0.194 | 0.237 | 0.304 | 0.425 | 0.706 |
| | 20 | 0.082 | 0.091 | 0.103 | 0.118 | 0.139 | 0.169 | 0.217 | 0.303 | 0.502 |
| | 25 | 0.059 | 0.066 | 0.074 | 0.085 | 0.100 | 0.122 | 0.156 | 0.218 | 0.316 |
| | 30 | 0.043 | 0.048 | 0.054 | 0.062 | 0.073 | 0.089 | 0.113 | 0.158 | 0.261 |
| | 35 | 0.032 | 0.036 | 0.040 | 0.046 | 0.054 | 0.065 | 0.083 | 0.115 | 0.190 |
| | 40 | 0.024 | 0.026 | 0.030 | 0.034 | 0.040 | 0.048 | 0.061 | 0.084 | 0.139 |
| | 45 | 0.018 | 0.020 | 0.022 | 0.025 | 0.029 | 0.035 | 0.045 | 0.062 | 0.101 |
| | 50 | 0.014 | 0.015 | 0.017 | 0.019 | 0.022 | 0.026 | 0.033 | 0.045 | 0.074 |

INHALER

BACKGROUND OF THE INVENTION

1. Field of the Invention

The present invention relates to an inhaler which ejects medicine, aroma, nicotine or the like as liquid droplets and allows a user to inhale.

2. Related Background Art

In recent years, medical and science advances have increased average lifetime, thus having created an aging society. Conversely, discovery of new diseases or infections due to changes in dietary life or life environment, environmental pollution, virus, bacteria or the like has increased people's health anxiety. Especially, countries called advanced countries have problems of increases in patients who have adult diseases such as diabetes mellitus or hypertension and need for improvement of medical cure.

For example, a patient who has diabetes mellitus, above all, insulin-dependent diabetes mellitus called I type must have insulin regularly administered because insulin is not secreted from the pancreas. The administration of insulin has been presently performed with hypodermic injection, which places physical and mental burdens on a user. To relieve the burdens onto the user, pen type injection syringes having a fine needle which will not give high pains have been also developed. However, many patients who have I-type diabetes mellitus have the same life as healthy people, except when insulin is required to be regularly administered. Accordingly, mental resistance against injection administration in public even with a pen type will make it difficult to perform administration at an appropriate time. Thus, such a method has a possibility of no implementation of appropriate procedures to users.

On the other hand, a method of taking medicine by user's inhalation through an inhaler has been developed as another resolution. Such medicine administration through a respiratory system will cause no pain during injection. As an example of the inhaler, there have been known inhalers using a principle of ink jet type for an ejection device (see International Publication Nos. WO1995/001137 and WO2002/004043).

Such inhalers require accurate control of the amount and interval of medicine administration according to prescription, appropriate ejection control and highly efficient medicine administration. For example, the diameter of liquid droplet of medicine at a suction port of the inhaler (a portion which is put in a user's mouth to inhale medicine) has an effect on a probability of reaching the lung alveoli. Accordingly, it is preferable to use an inhaler capable of attaining liquid droplets having a constant droplet diameter regardless of use environments. Ejected droplets of medicine are carried to suction port side on air flows generated by inhalation. Accordingly, it is common that water moisture is evaporated from the liquid droplets until the droplets reach the suction portion and the diameter of liquid droplet decreases. However, the inhaler is used under various environments different in humidity or temperature, and the amount of water vaporization from the ejected liquid droplets changes with a use environment. In other words, even if respective liquid droplets having a same diameter are always ejected, the diameter of the liquid droplet at the suction port may change with a use environment, which may be a cause for difficulty in performing inhalation of an appropriate dose prescribed by a doctor. As a resolution to solve such problems, there has been conventionally proposed an inhaler having a function of promoting evaporation using a heater and a dehumidifier and keeping the diameter of a liquid droplet constant (see International Publication No. Number WO1996/009846). As another resolution for promoting evaporation, there has been proposed an inhaler which extends an air flow path of a mouthpiece (see International Publication No. WO2000/024362).

Because a patient who has I-type diabetes mellitus requires regular administration, such an inhaler is always carried. Accordingly, the inhaler should be capable of inhaling liquid droplets having a constant diameter regardless of use environments and be of a small and lightweight type.

However, the inhaler disclosed in International Publication No. WO1996/009846 requires a heater and a dehumidifier as a gas generator for promoting vaporization. Provision of all energy for driving the inhaler in the inhaler in view of portability requires inclusion of energy consumed in the generator, which is a cause for increasing the size and weight of the inhaler.

The inhaler disclosed in International Publication No. WO2000/24362 has not clearly described based on what variable, an air flow path length of a mouthpiece should be controlled, in extending the mouthpiece flow path, in order to control a change in a droplet diameter with evaporation.

SUMMARY OF THE INVENTION

It is an advantage of the present invention to provide a small lightweight inhaler capable of inhaling medicine as liquid droplets having a constant diameter respectively, regardless of use environments.

To attain the foregoing advantage, the inhaler of the present invention is an inhaler for making a user inhale medicine from a suction port and includes: an air flow path connected with the suction port and for passing the medicine through; an opening mounted with a medicine ejection portion for ejecting the medicine and formed at a part of the air flow path so that the ejected medicine is ejected in the air flow path; a flow path length determining portion for determining a distance from the opening to the suction port according to use environments in using the inhaler; and a flow path length adjustable mechanism capable of changing the distance from the opening to the suction port.

The inhaler according to the present invention is configured as described above, which provides advantages described as follows:

Changing a distance from an opening to a suction port in an air flow path according to use environments in using the inhaler can change a flying period of liquid droplets, thus sucking liquid droplets each of which has a constant droplet diameter, regardless of use environments.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

FIG. 1 is a schematic perspective view illustrating an inhaler according to a first embodiment of the present invention.

FIG. 2 is a schematic perspective view illustrating a state in which an access cover for the inhaler illustrated in FIG. 1 is open.

FIG. 3 is a schematic perspective view of a medicine cartridge for the inhaler illustrated in FIG. 1.

FIG. 4 is a schematic longitudinal sectional view of the inhaler illustrated in FIG. 1.

FIG. 5 is a table illustrating a relationship between humidities and temperatures of use environments and an air flow length.

DETAILED DESCRIPTION OF THE PREFERRED EMBODIMENTS

Preferred embodiments of the present invention will now be described in detail in accordance with the accompanying drawings.

First Embodiment

Figure 1:
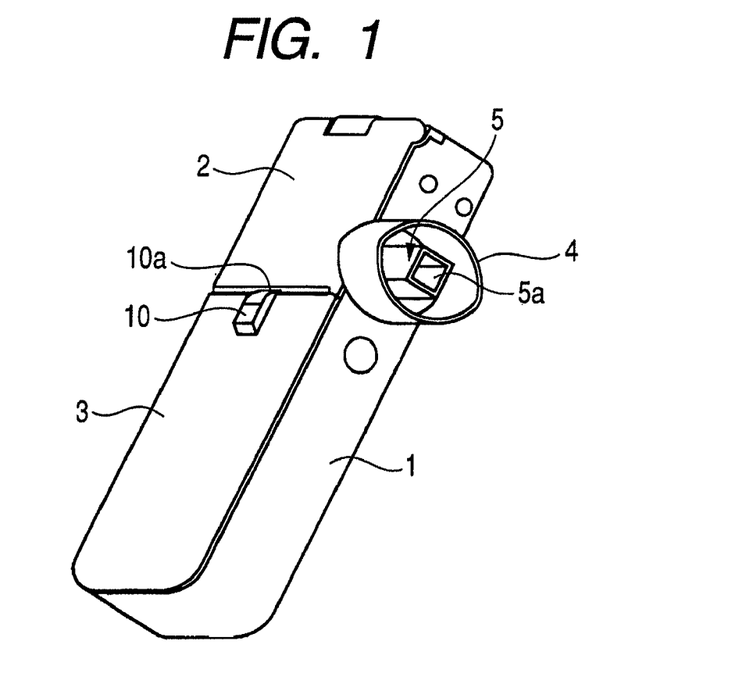

As illustrated in FIG. 1, at an open surface of a box-like housing body 1, there are disposed a front cover 3 and an access cover 2.

The front cover 3 is integrally formed so as to close one end of the open surface of the housing body 1 in the lengthwise direction. The access cover 2 is rotatably fitted on the other end of the open surface of the housing body 1 in the lengthwise direction through a hinge 2a and is forced in an always open direction by a return spring (not illustrated). At the front cover 3, there is disposed a lock lever 10 having a protrusion portion 10a engaging with one end (a free end) of the access cover 2 to prevent the access cover 2 from opening carelessly.

When the lock lever 10 is slid against a spring force, the protrusion portion 10a comes off the one end of the access cover 2, so that the spring force of the return spring allows the access cover 2 to rotate around a hinge axis (not illustrated) for opening.

Figure 2:
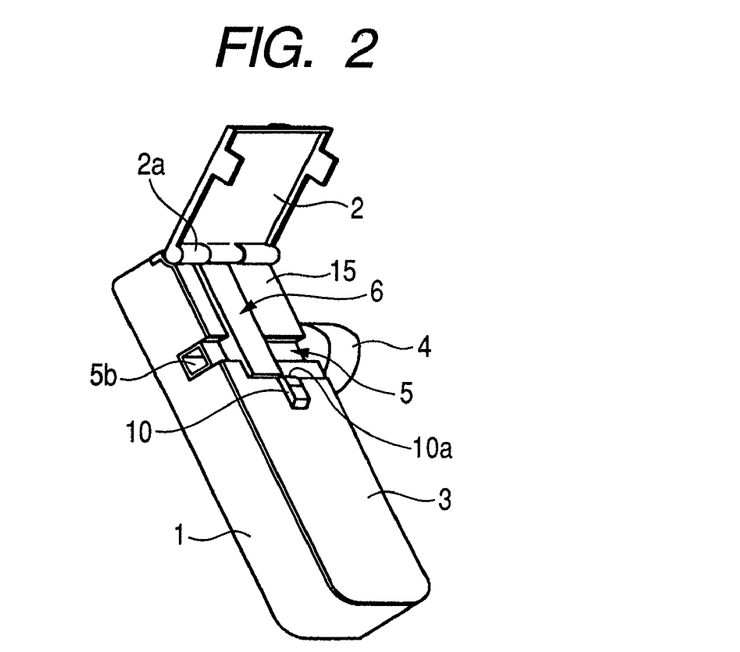

As illustrated in FIG. 2, when the access cover 2 opens, there is seen a medicine cartridge 6 which is formed by integrating an ejection head 8 as a medicine ejection portion for ejecting medicine and a reservoir 7 for storing medicine with each other. Additionally, the medicine cartridge 6 and a mouthpiece 4 are supported so as to be detachable to a guide portion 15 of the housing body 1. The mouthpiece 4 is formed with a suction port 5a and an air flow path 5 is formed by connecting the suction port 5a of the mouthpiece. The medicine ejected from the ejection head 8 passes through the air flow path 5 and is led to the suction port. When a user performs inhalation, air enters from an intake port 5b and air flow is generated in the air flow path 5, thus placing the ejected medicine on the air flow.

Figure 3:
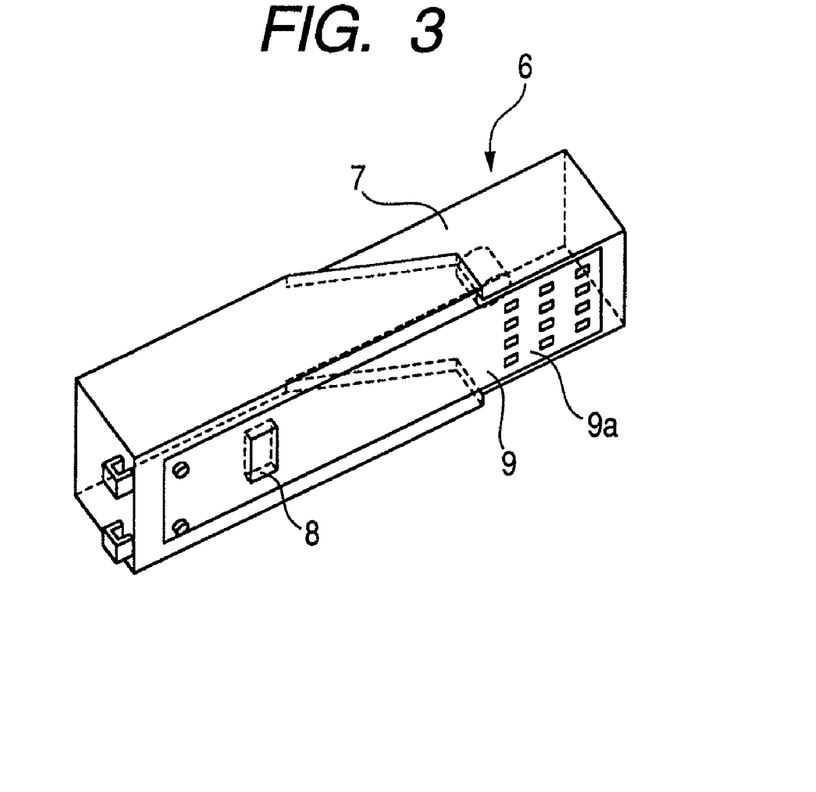

FIG. 3 is a schematic perspective view of a medicine cartridge 6. The medicine cartridge 6 includes: the reservoir 7 for storing medicine; the ejection head 8 for ejecting the medicine supplied from the reservoir 7 as liquid droplets; and a member 9 having an electrical connection face 9a with a battery 18 for supplying electric power to an ejection energy generating element provided at the ejection head 8. The battery 18 uses chargeable secondary cells.

In the present invention, the medicine ejection portion (an ejection head) has any ejection energy generating element. As the ejection energy generating element, an electrothermal transducer for providing thermal energy or an electromechanical transducer for providing mechanical energy to medicine may be exemplified. Specifically, as an ejection method for medicine, there is exemplified a method for providing thermal energy to medicine with the electrothermal transducer and ejecting the medicine from an ejection port (a thermal jet system) or a method for ejecting medicine from the ejection port using a vibrating pressure of the electromechanical transducer, such as a piezoelectric element, for providing mechanical energy to medicine. An ejection method can be selected according to types of medicines.

For use of the thermal jet system, individual liquid ejection units can provide a large quantity of heat pulse according to a bore diameter of an ejection port and used for ejection as well as high size precision and reproductivity of a micro heater, thus attaining distribution of a small liquid droplet diameter. Further, high applicability to small apparatuses which require low head manufacturing cost and frequent head replacement are also attainable. Accordingly, in a medicine ejection apparatus which requires high portability or convenience, especially, a thermal jet type ejection apparatus is preferable.

In the present invention, the ejection head 8 may use a medicine ejection cartridge in the form of a single body integrated with the reservoir 7 as illustrated in FIG. 3 or use a configuration separated from a reservoir.

Figure 4:
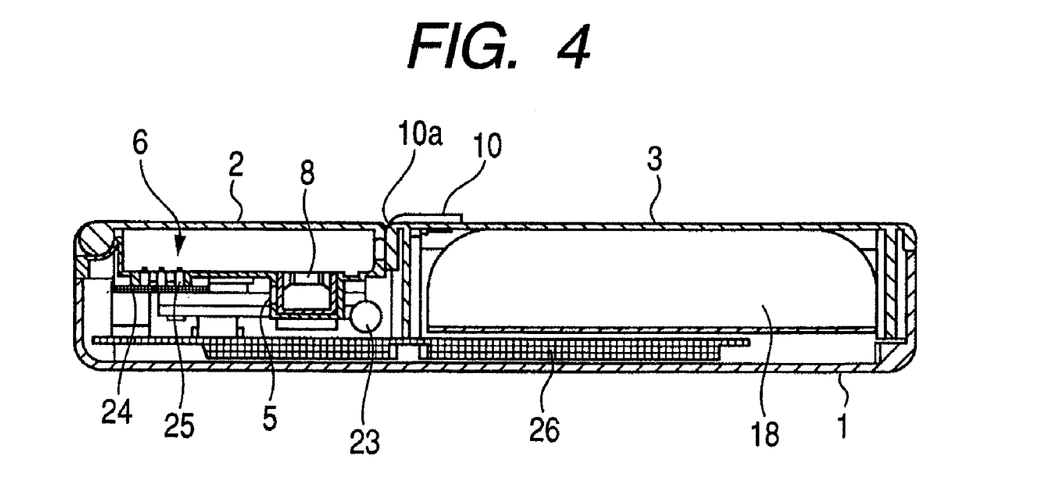

FIG. 4 is a schematic longitudinal sectional view of the inhaler illustrated in FIG. 1. In the housing body 1, there are disposed a battery 18, a control substrate 26 and a probe substrate 24 electrically connected with the control substrate 26 through a cable or a connector. The probe substrate 24 is formed with a contact probe 25 for energizing the electrical connection face 9a of the medicine cartridge 6.

In a space between the battery 18 and the mouthpiece 4, a vibrating motor 23 is disposed so as to contact the control substrate 26. This allows commence of suction and, when a flow rate of sucked air reaches an ejectable region, liquid droplets starts to eject and at the same time, the vibrating motor 23 starts to vibrate, which notifies a user that ejection has started. A pressure sensor 120 (see FIG. 12) provided in the air flow path 5 detects a negative pressure generated in the air flow path 5 by user's inhalation, thus attaining a user's inhalation profile. To inhale an inhalation amount for backup based on an inhalation speed calculated from a measurement of the pressure sensor 120 so that the last liquid droplet reaches the lungs after completion of ejection of a predetermined amount of liquid droplets, the vibrating motor 23 vibrates for a backup inhalation time even after the completion of ejection and urges a user to inhale medicine so that the medicine has completely reached the lungs. Upon completion of the vibration of the vibrating motor 23, the patient stops the inhalation.

Figure 6:
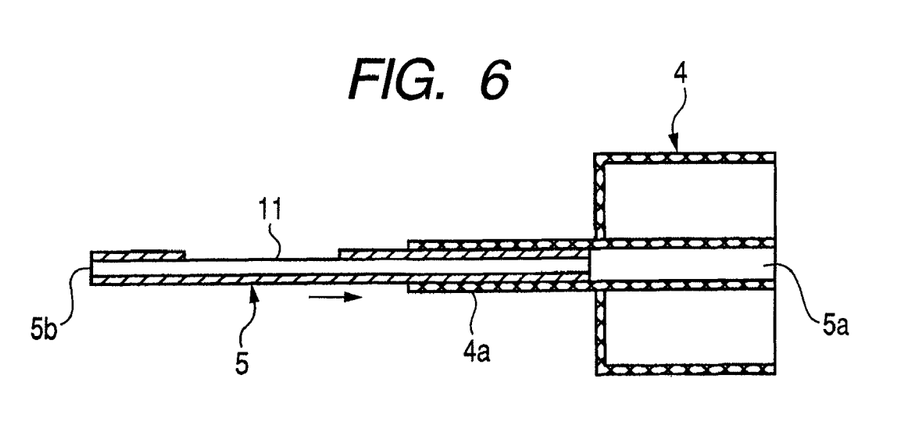
FIG. 6 is a schematic cross sectional view of a flow path length adjustable mechanism for the inhaler illustrated in FIG. 1.

FIG. 6 is a schematic cross sectional view of a flow path length adjustable mechanism for the inhaler according to the first embodiment. As illustrated in FIG. 6, the flow path adjustable mechanism includes a second flow path forming member 5 expandably fitted, in an axial direction, into a first flow path forming member 4a having a suction port 5a. At a part of the second flow path forming member 5, an opening 11 is formed so that the liquid droplets ejected from the ejection head 8 are ejected into the air flow path. The opening 11 is attached with the medicine cartridge 6 so that the ejection head 8 faces. A distance from the opening 11 to the suction port 5a can be changed by axially sliding the first flow path forming member 4a and the second flow path forming member 5. The distance from the opening 11 to the suction port 5a is sometimes referred to as a "flow path length".

Now, description will be made on a flow path length determining portion for determining the distance from the opening 11 to the suction port 5a according to use environments in using the inhaler.

Figure 5:
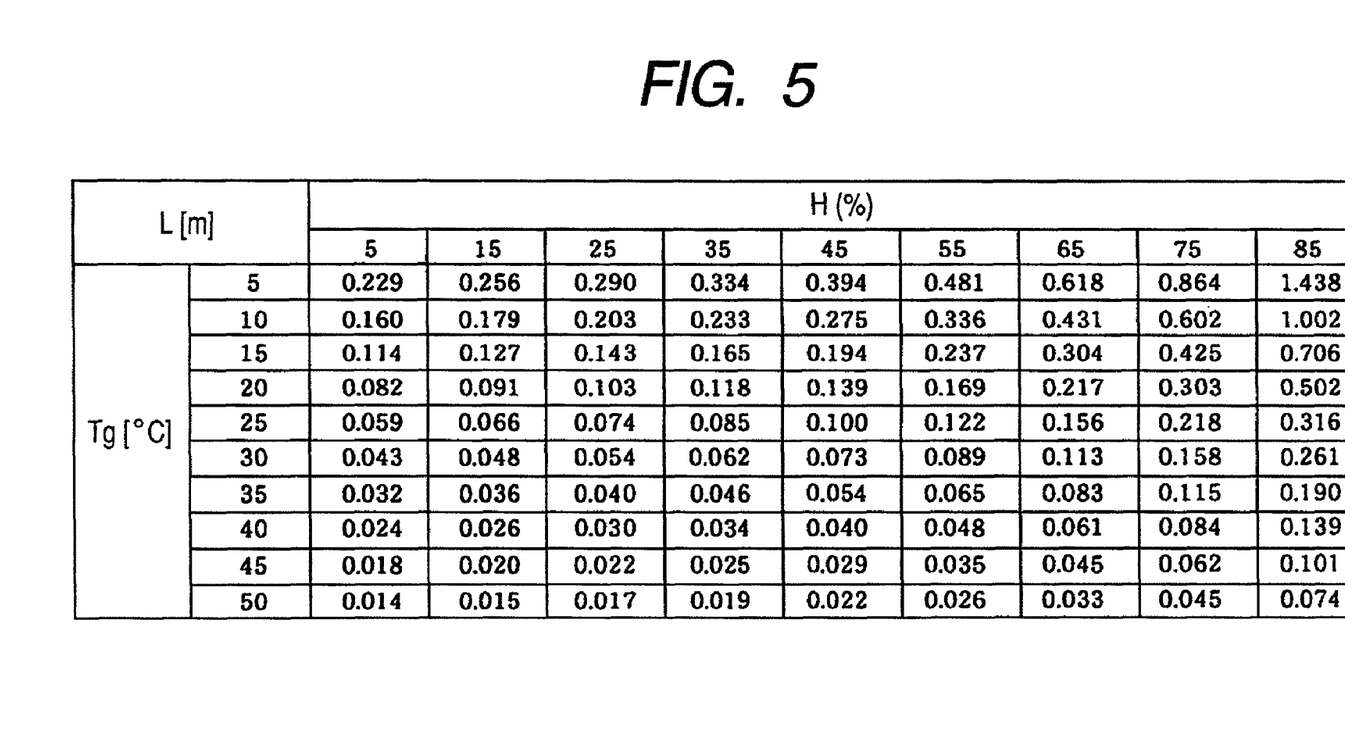
Figure 8:
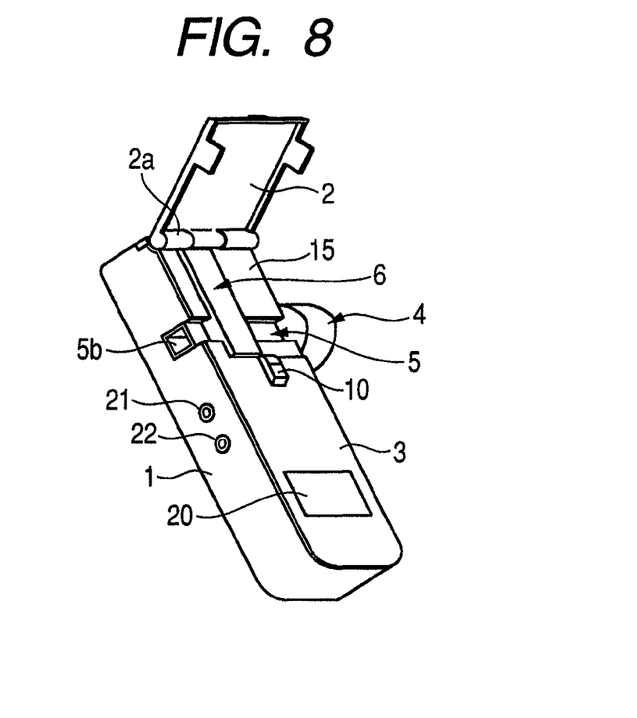
FIG. 8 is a schematic perspective view illustrating a state in which an access cover of an inhaler according to a third embodiment of the present invention is open.

FIG. 5 is a table illustrating a relationship between humidities and temperatures of use environments and a flow length. The illustrated values are the values obtained by estimating an air flow path length required for each of water droplets having a diameter of 6 µm to change into 3 µm, on the assumption that a flow rate of air flow is 10 m per second, temperatures are unchangeable and a space is uniform. The inhaler of the present invention, storing such a table in CPU, includes a device for determining an appropriate air flow path length under use environments in using the inhaler by checking measurement results of humidities and temperatures under use environments against the table. Humidities and temperatures, as illustrated in FIG. 8, may be measured using an inhaler equipped with a thermometer and a hygrometer, but are not limited thereto. For example, a user may also use an inhaler of such a type capable of inputting use environments such as temperature and humidity.

TABLE 1 indicates a relationship between a flow rate of air flow and diameters of droplets in a flying distance (X). The relationship has been made on the assumption that approx. 2,000,000 droplets, each of which has a diameter of 3 µm under a temperature of 20° C. and a humidity of 33%, are ejected per second. The table indicates that changes in the diameters of liquid droplets have effects on flow rates of air flow above a certain level. Accordingly, there will exist a table (namely, a 3D table) indicating a relationship between humidities, temperatures and air flow path lengths under use environments as illustrated in FIG. 5 at respective flow rates of air flow. Determination of an air flow path length by adding effects of flow rates of air flow on air flow path lengths can highly precisely keep diameters of liquid droplets to be inhaled constant. The flow rate of air flow can be measured using the pressure sensor 120. Moreover, a flow meter may be used in place of the pressure sensor.

TABLE 1

| Flow rate of air flow (m/s) | X = 3 cm | X = 6 cm | X = 9 cm | X = 12 cm | X = 15 cm |
|---|---|---|---|---|---|
| 5 | 2.7 | 2.4 | 2.2 | 2.1 | 2.0 |
| 10 | 2.6 | 2.3 | 2.0 | 1.8 | 1.5 |
| 15 | 2.6 | 2.3 | 1.9 | 1.6 | 1.1 |

Possible parameters of causes for changes in diameters of liquid droplets are diameters of liquid droplets during ejection and driving frequencies of the ejection head 8. Preferable conditions can be determined, provided that a prescription for medicine to be inhaled has been determined. Accordingly, if the ejection conditions inherent in an apparatus have been determined, it is sufficient to consider only humidities and temperatures of use environments and parameters dependent on external environments such as flow rate of air flow.

Second Embodiment

Figure 7:
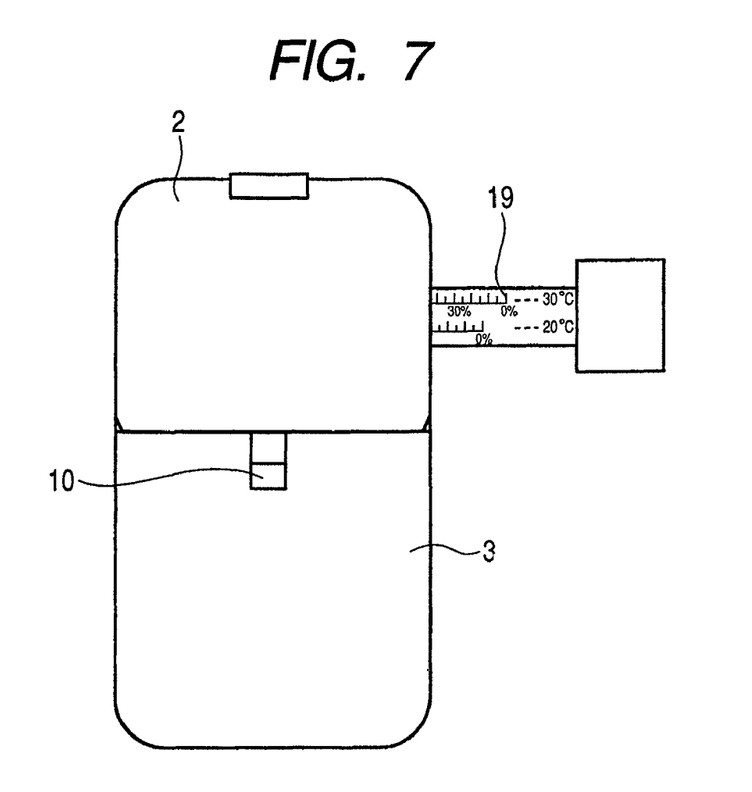
FIG. 7 is a schematic front view of an inhaler according to a second embodiment of the present invention.

FIG. 7 is a schematic front view of an inhaler according to a second embodiment of the present invention. In a second embodiment, a relationship between expansion amounts of an air flow path 5 and ambient humidities and temperatures of use environments is indicated on an outer surface of the air flow path 5 as a graduation 19. For example, a relationship between humidities and expansion amounts at temperatures of 20° C. and 30° C. This enables a user to adjust an air flow path length for obtaining an appropriate evaporation amount according to humidities and temperatures of use environments.

Third Embodiment

FIG. 8 is a schematic perspective view illustrating a state in which an access cover of an inhaler according to a third embodiment of the present invention is open. An inhaler according to a third embodiment is attached with a humidity measurement function and a temperature measurement function. The humidity measurement function and the temperature measurement function are implemented, for example, by attaching a hygrometer 21 and a thermometer 22 onto the inhaler, by which measurement is made upon turning-on of an inhaler power switch. The measurement results are converted into electrical information and are displayed on a liquid crystal unit 20 as a display unit (a display portion) provided on the inhaler. These functions enable a user to adjust an air flow path length of the air flow path using a function included in the inhaler.

Fourth Embodiment

Figure 9:
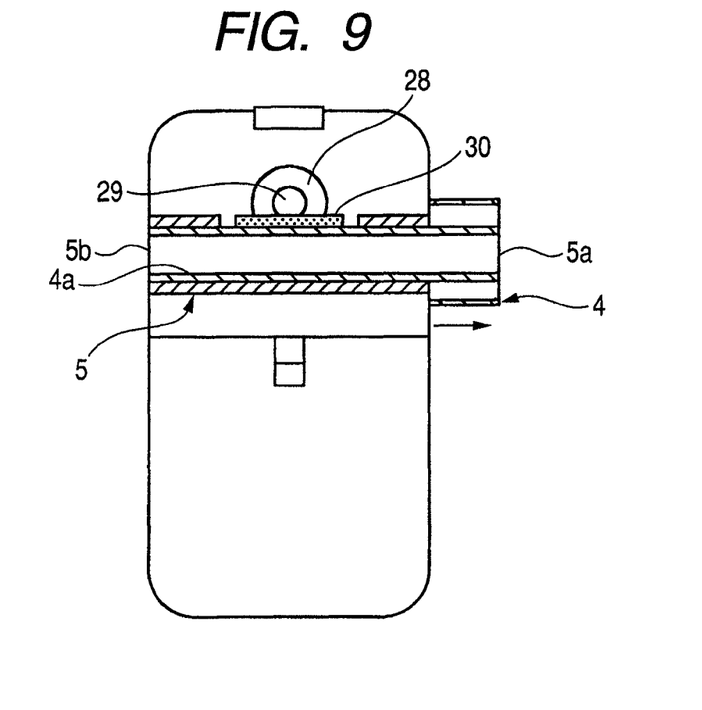
FIG. 9 is a schematic cross sectional view of a flow path length adjustable mechanism for an inhaler according to a fourth embodiment of the present invention.

FIG. 9 is a schematic cross sectional view of a flow path length adjustable mechanism for an inhaler according to a fourth embodiment of the present invention. A flow path length adjustable mechanism used in an inhaler according to a fourth embodiment is configured so that one flow path forming member 4a provided at a mouthpiece 4 has the other flow path forming member 5 expandably fitted in the axial direction. An outer side surface of the other flow path forming member 5 is integrally formed with a rack 30. A pinion 29 engaged with the rack is rotated in the forward and rearward directions by a motor 28 to make an expansion in illustrated arrowhead and non-arrowhead directions. Specifically, there is also provided a rack-pinion mechanism as a linear drive device for automatically expanding the one flow path forming member 4a and the other flow path forming member 5. Such a configuration provides a mechanism which automatically adjusts an air flow path to the air flow path length determined based on measurement results from a hygrometer 21 and a thermometer 22 mounted on the inhaler, as illustrated in FIG. 8.

In place of the rack-pinion mechanism according to the present embodiment, for example, a linear drive device such as fluid pressure cylinder or an electric cylinder may be used.

Fifth Embodiment

Figure 10:
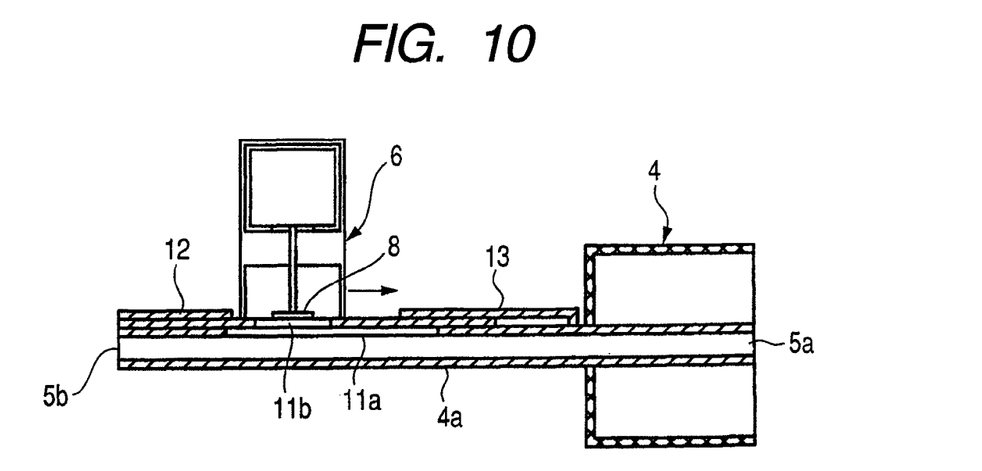
FIG. 10 is a schematic cross sectional view of a flow path length adjustable mechanism for an inhaler according to a fifth embodiment of the present invention.

FIG. 10 is a schematic cross sectional view of a flow path length adjustable mechanism for an inhaler according to a fifth embodiment of the present invention. As illustrated in FIG. 10, a flow path adjustable mechanism according to a fifth embodiment is formed with a flow path forming member 4a provided at a mouthpiece 4 put in a user's mouth. A boundary plate 12 for covering a communication port 11a provided in a flow path forming member 4a from the outside is slidably disposed in the axial direction through a slide direction guide plate 13. The boundary plate 12 is formed with an opening 11b for guiding liquid droplets ejected from an ejection head 8. Movement of the boundary plate 12 according to the present embodiment in an illustrated arrowhead or a non-arrowhead direction can change a distance between the opening 11b and the suction port 5a.

Sixth Embodiment

Figure 11:
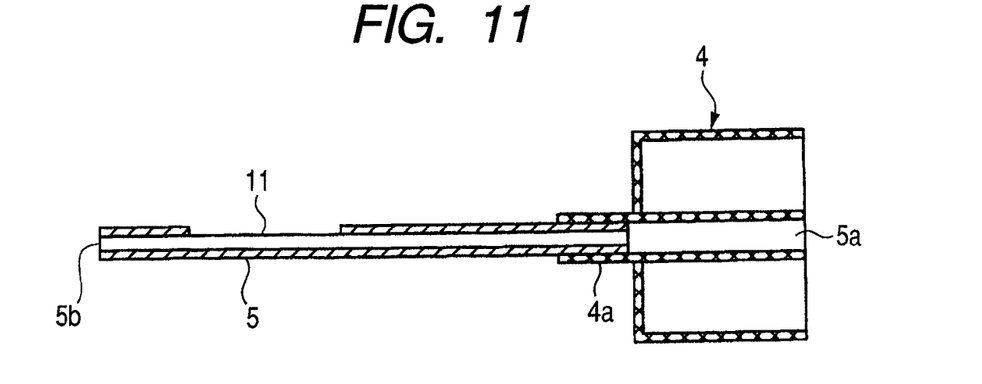
FIG. 11 is a schematic cross sectional view of a flow path length adjustable mechanism for an inhaler according to a sixth embodiment of the present invention.

FIG. 11 is a schematic cross sectional view of a flow path length adjustable mechanism for an inhaler according to a sixth embodiment of the present invention. In the present embodiment, a second flow path forming member 5 is exchangeably connected to a first flow path forming member 4a provided at a mouthpiece 4. The second flow path forming member 5 is connected to the one flow path forming member 4a so as to have an opening 11 at an axial portion corresponding to the air flow path length determined according to humidities and temperatures of a use environment of the inhaler. This can change an air flow path length, that is, a distance from the opening 11 to the suction port 5a.

Figure 12:
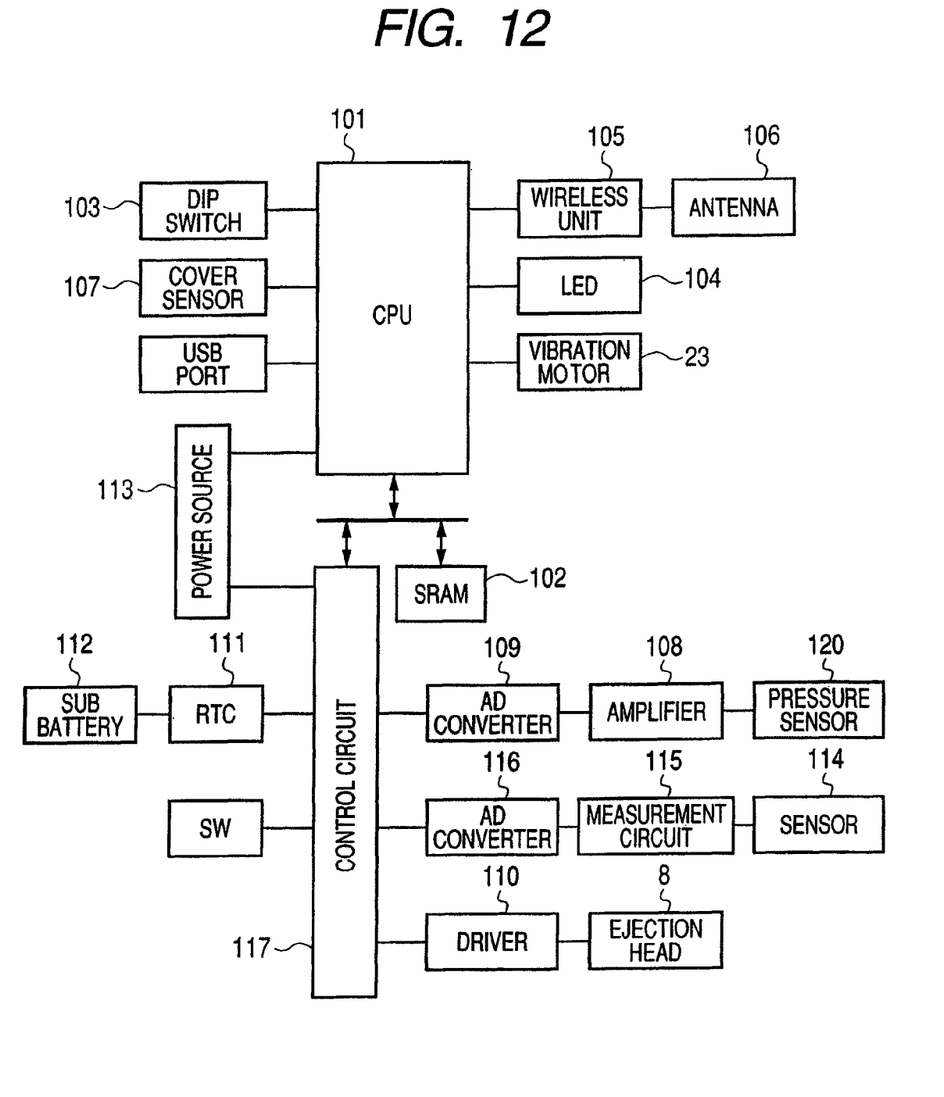
FIG. 12 is a block diagram illustrating a controller for the inhaler according to the present invention.

FIG. 12 is a block diagram illustrating a controller for the inhaler according to the present invention. Reference character 101 denotes a CPU as an arithmetic processing unit and stores a flash ROM storing programs. Reference character 102 denotes a SRAM as a readable/writable memory for temporarily storing data in operating the program. Reference character 103 denotes a dip switch connected with a port of the CPU and for setting ON/OFF information and fetching the information into the CPU 101. Reference character 104 denotes an LED as a display unit for notifying a user or a maintenance worker of a state of an apparatus. Reference character 105 denotes a wireless unit which transfers a state and a storage content of an apparatus to a host computer and controls wireless communication for receiving data from the host computer. Reference character 106 denotes an antenna for the wireless unit and reference character 107 denotes a cover sensor for detecting an opening/closing state of an access cover 2. Reference character 108 denotes an amplifier for level-converting and amplifying an output of a pressure sensor 120, and reference character 109 denotes an AD converter for converting an analog output of the amplifier 108 into a digital signal. Reference character 110 denotes a driver for controlling an ejection head 8, reference character 111 denotes an RTC having a calendar/clock function and reference character 112 denotes a backup sub battery for the RTC 111. Reference character 113 denotes a power source for developing various types of voltages supplied to an electric circuit and includes a main battery, a charge circuit, a reset circuit and a power switch. Reference character 114 denotes a sensor for detecting an inclination of the inhaler and reference character 115 denotes a measurement circuit for processing an output of the sensor 114. Reference character 116 denotes an AD converter for converting an analog signal as an output of the measurement circuit 115 into a digital signal. Reference character 117 denotes a control circuit which processes an output or input signal for various types of blocks and is connected with a CPU 101 through a bus.

Operating the power switch permits the power source 113 to output a reset signal to CPU 101, so that the signal initializes the CPU 101, which starts an operation according to the program stored in the internal flash ROM and fetches a state of the dip switch 103 and, if no special setting is made, an operation starts as an ordinary operation mode. A user's inhalation changes an output of the pressure sensor 120 and the change is transmitted to the CPU 101 through the amplifier 108, the AD converter 109 and the control circuit 117. When the inhalation amount exceeds a predetermined threshold value, the CPU applies a voltage to the vibrating motor 21 to start the vibration and transmits a pulse signal to the ejection head 8 through the control circuit 117 and the driver 110, thus ejecting the medicine included in the medicine ejection unit. After the ejection is performed for a defined period, the vibration continues for a defined period and, during the period, a user is urged to perform inhalation. In the course of the series of operation, the CPU 101 sequentially monitors information of the sensor 114 and, when the inclination information exceeds a certain threshold value, changes a controlled variable for the ejection head 8 through the control circuit 117, thus controlling the diameter of the liquid droplets ejected by the ejection head 8. Further, when the inclination exceeds a second threshold value, the CPU 101 changes a vibrating pattern of the vibrating motor 21 and instructs a user to make no larger inclination than the second threshold value.

The present invention is not limited to the above embodiments and various changes and modifications can be made within the spirit and scope of the present invention. Therefore to apprise the public of the scope of the present invention, the following claims are made.

This application claims the benefit of Japanese Patent Application No. 2007-055023, filed Mar. 6, 2007, which is hereby incorporated by reference herein in its entirety.

What is claimed is:

1. An inhaler for making a user inhale medicine from a suction port comprising:
    an air flow path connected with the suction port and for passing the medicine through;
    an opening mounted with a medicine ejection portion for ejecting the medicine and formed at a part of the air flow path so that the ejected medicine is ejected in the air flow path;
    a flow path length determining portion for determining a distance from the opening to the suction port according to use environments in using the inhaler; and
    a flow path length adjustable mechanism capable of changing the distance from the opening to the suction port.

2. The inhaler according to claim 1, comprising a display portion for displaying measurements of the use environments.

3. The inhaler according to claim 1, wherein the air flow path is formed by connecting a first flow path forming member having the suction port with a second flow path forming member having the opening and the flow path length adjustable mechanism is configured so that the first flow path forming member and the second flow path forming member are slidable.

4. An inhaler for making a user inhale medicine from a suction port comprising:
    an air flow path connected with the suction port and for passing the medicine through;
    an opening mounted with a medicine ejection portion for ejecting the medicine and formed at a part of the air flow path so that the ejected medicine is ejected in the air flow path;
    a flow path length determining portion for determining a distance from the opening to the suction port according to humidities and temperatures of use environments in using the inhaler; and
    a flow path length adjustable mechanism capable of changing the distance from the opening to the suction port.

5. An inhaler for making a user inhale medicine from a suction port comprising:
    an air flow path connected with the suction port and for passing the medicine through;

an opening mounted with a medicine ejection portion for ejecting the medicine and formed at a part of the air flow path so that the ejected medicine is ejected in the air flow path;

a flow path length determining portion for determining a distance from the opening to the suction port according to humidities and temperatures of use environments in using the inhaler and the flow rate of an air flow generated in the air flow path; and a flow path length adjustable mechanism capable of changing the distance from the opening to the suction port.

* * * * *